United States Patent [19]

Elgebaly

[11] Patent Number: 5,403,914

[45] Date of Patent: Apr. 4, 1995

[54] BIOLOGICAL MEDIATORS OF IMMUNE FUNCTIONS

[75] Inventor: Salwa A. Elgebaly, Bloomfield, Conn.

[73] Assignee: The University of Connecticut, Farmington, Conn.

[21] Appl. No.: 975,640

[22] Filed: Nov. 13, 1992

Related U.S. Application Data

[63] Continuation-in-part of Ser. No. 852,890, Mar. 17, 1992, abandoned, which is a continuation of Ser. No. 649,154, Feb. 1, 1991, abandoned, which is a continuation of Ser. No. 107,280, Oct. 9, 1987, abandoned.

[51] Int. Cl.⁶ .................... A61K 37/02; C07K 5/00; C07K 7/00; C07K 15/00
[52] U.S. Cl. .................... 530/324; 530/328; 530/350; 530/387.1; 424/569
[58] Field of Search .................... 424/569; 514/2, 21; 530/324, 328, 350, 387.1

[56] References Cited

U.S. PATENT DOCUMENTS 4,797,277 1/1989 Arfors .................... 514/21

OTHER PUBLICATIONS

Elgebaly et al., Eleventh Int. Res. Congress, Oct. 17–21, 1987.
Kozol et al., American Gastroenterological Asso., "Gasteric-Derived Leukocyte Chemotactic Factors: Initial Characterization" May 10–13, 1987.
Elgebaly et al., AJP, pp. 40–50, 1987.

*Primary Examiner*—Robert J. Hill, Jr.
*Assistant Examiner*—Sheela J. Huff
*Attorney, Agent, or Firm*—Chilton, Alix & Van Kirk

[57] ABSTRACT

A chemotactic factor released from tissue in response to injury represents the initial signal that recruits neutrophils to the tissue. As released, the factor exists as a positively charged protein complex consisting of a low molecular weight active peptide factor that carries a neutral to negative charge and a weakly associated high molecular weight protein. The tissue derived complex exhibits a molecular weight of about 100,000–300,000 daltons and the factor is obtained therefrom and purified. The peptide factor is non-immune cell derived and non-serum derived and exhibits a molecular weight of approximately 3,000 daltons.

11 Claims, 7 Drawing Sheets

BIOLOGICAL MEDIATORS OF IMMUNE FUNCTIONS

RELATED APPLICATIONS

This application is a continuation in part of my application Ser. No. 07/852,890, filed Mar. 17, 1992, now abandoned, which is a continuation of application Ser. No. 07/649,154, filed Feb. 1, 1991, now abandoned, which is a continuation of application Ser. No. 07/107,280, filed Oct. 9, 1987, now abandoned.

BACKGROUND OF THE INVENTION

The present invention relates generally to a family of biological mediators of immune function associated with nonphysiological conditions. More specifically, it is concerned with purified and isolated leukocyte chemotactic factors released from injured tissue.

Biological mediators such as leukocyte chemotactic factors stimulate the migration of neutrophils from circulation into sites of infection or tissue damage. These mediators are also believed to increase cell adhesion to injured sites and to activate neutrophils to release toxic agents such as oxygen metabolites and proteases. Due to these beneficial characteristics, the nature and source of these mediators have been extensively studied. It has been believed they are primarily derived from low molecular weight serum protein components, that is, from complement-split products C3a and C5a and fibrin-split peptide products as well as from activated immune cells such as leukotriene B4, LTB4, and interleukin-8, IL-8. Type I collagen and the synthetic tripeptide f-Met-Leu-Phe are also chemotactically active for both neutrophils and mononuclear cells.

The mechanism for neutrophil recruitment associated with tissue injury is not clear. Serum-derived leukocyte chemotactic factors, such as activated complement components C3a and C5a, have been suggested as playing a role in such a process. Specifically, the interrelationship between ischemic myocardial tissue and inflammatory cells has led to the suggestion that the chemical recruitment signal attracting the neutrophils into infarcted myocardium may be the result of one or more of the following four mechanisms:

1) Serum-derived C3a that is generated from the interactions of tissue protease found in myocardium and the third complement component,
2) Serum-derived C5a generated from the interactions of lysosomal granules of neutrophils that have responded to the initial chemotactic stimulus in the infarcted myocardium and the fifth complement component,
3) A superoxide-dependent factor generated from the interaction of superoxide radicals released by activated neutrophils and latent chemotactic factors present in extracellular fluids, or
4) Platelet-activated factors and arachidonic acid metabolites released by accumulated neutrophils.

To date, the initial signals that recruit and activate the neutrophils during ischemia have not been defined and it is not known whether injured tissue directly participates in the influx of circulating leukocytes by releasing mediators which recruit neutrophils to the sites of the injury.

SUMMARY OF THE INVENTION

It has now been found, in accordance with the present invention, that high levels of chemotactic factors are released from tissue such as coronary arteries and myocardial tissue under ischemic conditions. These neutrophil chemoattractants released under ischemic conditions are believed to represent the initial signal that recruits neutrophils to the tissue shortly after ischemia. They differ in their biochemical characteristics and molecular weight from previously known factors, such as the complement split products C3a and C5a having molecular weights of about 11,000 daltons and leukocyte products such as IL-8 and LTB4 that have molecular weights of 10,000 daltons and 366 daltons, respectively. As released from the tissue, the factors exist as protein complexes having a molecular weight of about 100,000 to 300,000 daltons. The complexes are positively charged units consisting of a weakly associated high molecular weight co-factor or carrier and a low molecular weight, less than 5,000 daltons, active factor that carries a neutral or negative change. The previously known factors C3a, C5a, IL-8 and LTB4 appear to play important roles as late signals that recruit additional neutrophils to infarcted myocardium and to regions where neutrophils exist, such as inflamed myocardium.

Accordingly, it is an object of the present invention to provide a new family or group of protease sensitive factors that are released from stressed tissue such as ischemic heart and arterial tissue as weakly associated complexes and that have a potent effect on the stimulation of neutrophil function. Included in this object is the provision for a new low molecular weight factor and weakly associated high molecular weight complexes thereof derived from myocardial and coronary arterial tissue that affect neutrophil migration and activation.

Another object of the present invention is to provide a new protein-like factor or factors of the type described that will allow better clinical management of patients with cardiovascular inflammation or undergoing heart surgery, organ transplant, or similar procedures and facilitate new approaches to vascular therapy through the control and regulation of the recruitment and activation of neutrophils associated with acute inflammatory reactions.

A further object of the present invention is to provide a new and improved mediator of the type described that is found in a variety of tissues and in various species, the mediators being tissue specific and capable of signaling the initial stressed condition of the tissue to stimulate neutrophil migration to the infarcted area particularly during subsequent reperfusion following open heart surgery, organ transplant, and the like.

A still further feature of the present invention is the provision for a new and improved procedure for concentrating, isolating, and at least partially purifying the neutrophil chemotactic factors of both the complex and its dissociated components from injured tissue such as ischemic myocardial and coronary arterial tissue. Included in this is the provision for the concentration, purification and isolation of chemotactic factors that differ from known neutrophil chemotactic factors, are not released from serum or white blood cells and are of a molecular weight that is significantly different from the molecular weight of known factors such as those mentioned heretofore. This neutrophil chemoattractant advantageously differs in its biochemical characteristics and is believed to play an important role in leukocyte infiltration associated with tissue inflammation and repair.

Another object of the present invention is to provide a new and improved inflammatory mediator for myocardial and/or coronary arterial tissue that is released under ischemic conditions, that is, under conditions of nonspecific injury, to provide in the absence of serum and immune cells a neutrophil chemoattractant that stimulates the migration of circulating leukocytes into injury sites. This new mediator differs in its biochemical characteristics from serum-derived and cell-derived factors.

Other objects and advantages will be in part obvious and in part pointed out more in detail hereinafter.

These and related objects are achieved in accordance with the present invention by providing a purified and isolated biological mediator comprising a high molecular weight neutrophil chemotactic factor protein complex released and concentrated from injured tissue such as ischemic coronary and myocardial tissue and consisting of an active low molecular weight factor weakly associated with a high molecular weight co-factor carrier. The factors evidence a protein character, heat instability, and a molecular weight for the complex of about 100,000 to 300,000 daltons, with the molecular weight of the active component factor being less than 5,000 daltons. The factors are not extractable by organic solvents suggesting that the activity is not leukotriene dependent. Structure identification of these factors will provide a unique cardiovascular therapy approach by regulating the recruitment of neutrophils associated with myocardial inflammation and repair. The factors may be obtained in coronary artery and myocardial tissue by inducing ischemia to release significant chemotactic activity followed by initial separation and concentration of the factors. The concentrated factors are then purified and may be used to produce antibodies, markers and blockers.

A better understanding of the invention will be obtained from the following detailed description and the accompanying drawing as well as from the illustrative applications of the invention including the several components thereof and the relationship of one or more of such components with respect to each of the others as well as the features, characterisitics, compositions, properties and relation of elements described and exemplified herein.

DESCRIPTION OF A PREFERRED EMBODIMENT

The family of leukocyte chemotactic factors of the present invention may be generated and isolated by initially inducing a nonphysiological condition such as stress or injury to the tissue. While ischemia in myocardial and coronary tissue will be used herein for ease of understanding and clarity of description and illustration, it will be understood that the invention has application to other non-physiological conditions and to a variety of other tissues.

The ischemic condition may be induced in the cardiovascular tissue by clamping or other flow arresting means including perfusing or incubating intact or cut hearts or heart segments with freshly prepared crystalloid cardioplegia or phosphate buffer solution, PBS. For human studies, coronary sinus effluents were collected from patients undergoing aortocoronary bypass. Samples were collected prior to and during aortic cross-clamping as well as at fixed intervals after cross-clamping thereby excluding peripheral circulation and assuring sampling from only within the heart.

Perfusion of the animal hearts was performed under reduced flow according to standard procedure. Initial hydrostatic perfusion pressure above the aorta was 115 cm of water. For the first five minutes, hearts were perfused with Ringer's lactate to wash off remaining blood before switching to freshly prepared cardioplegia. The cardioplegia was freshly prepared crystalloid material to avoid nonspecific chemotactic activity due to bacterial contamination. Chemotactic activity was not detected if crystalloid cardioplegia was replaced by modified Ringer solution. The PBS had to be sterile to eliminate interference by bacterial contamination. A volume of cold, 4° C., non-oxygenated cardioplegia was used. At set time intervals, samples were removed to assay for the presence of neutrophil chemotactic factors and the level of chemotactic activity. At the end of the perfusion, the hearts were fixed for histologic evaluation. To control for non-specific factors generated during circulation, cold non-oxygenated cardioplegia was circulated for four hours in the absence of heart tissue.

Intact hearts were incubated with freshly prepared cardioplegia or PBS at 4° C. for the same time intervals. The release of neutrophil chemoattractants was similarly assayed in the supernatants of hearts singly cut longitudinally and heart segments.

Figure 1:
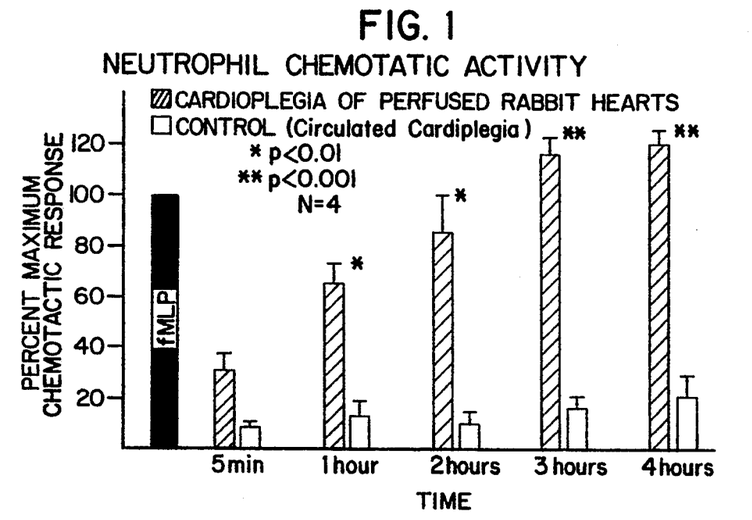
FIGS. 1, 2 and 3 are graphs showing neutrophil chemotactic activity in various tissues as a function of time and maximum chemotactic response.
Figure 2:
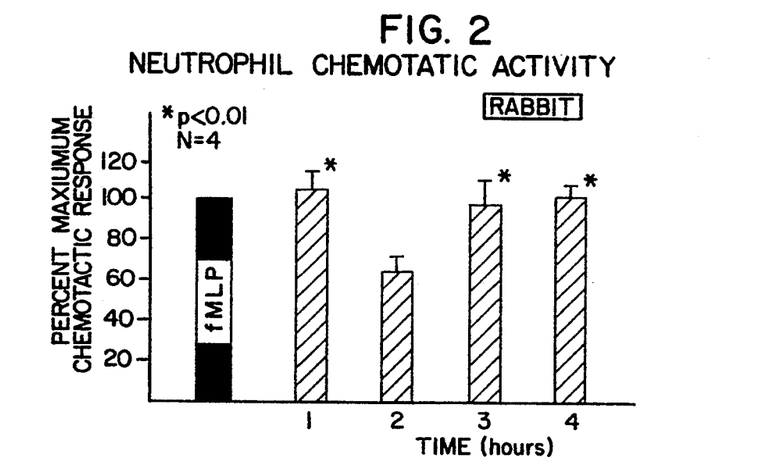
Figure 3:
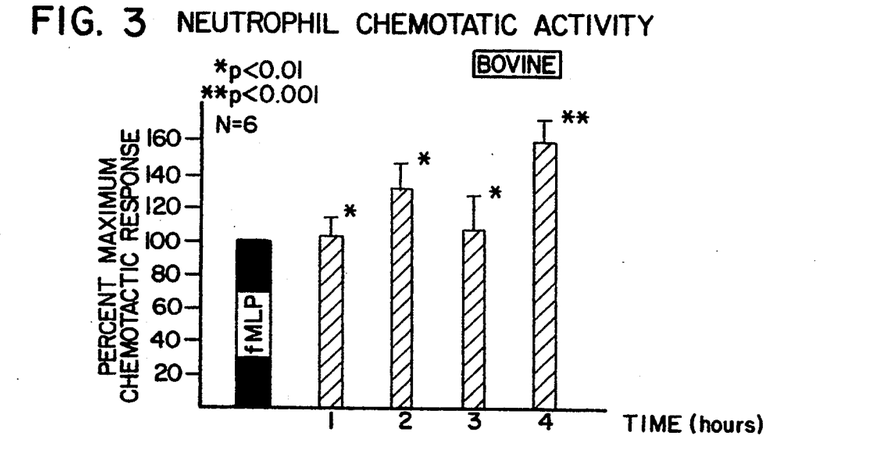
Figure 4:
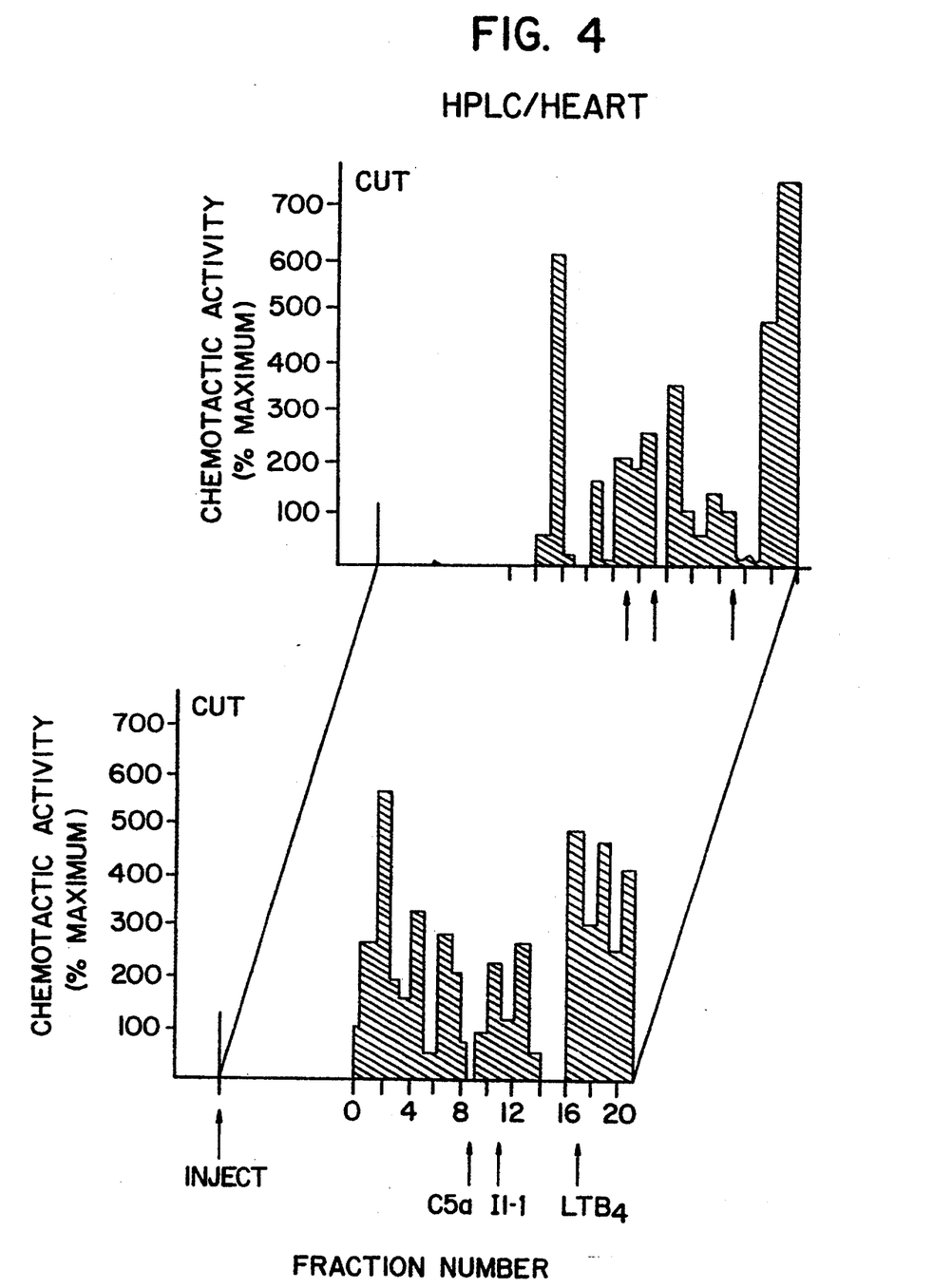
FIG. 4 graphically depicts the chemotactic activity of separated chromatographic fractions.

For determining whether neutrophil chemoattractants were released, myocardial segments were obtained from isolated rabbit, bovine and pig hearts. Typical results are shown graphically in FIGS. 1, 2 and 3. All data are expressed as mean values plus or minus the standard error of the mean. It was also determined that intact hearts kept at −20° C. for three to four months were able to release neutrophil chemotactic factors similar to fresh hearts.

Various test conditions showed high levels of neutrophil chemotactic factors released by the ischemic tissue. Hearts perfused with cold cardioplegia release significant chemotactic activity within three to four hours while control cardioplegia circulated without tissue shows low levels of activity, indicating that the detected activity is not a breakdown product of cardioplegia, but rather is released from the ischemic tissue. Histologic evaluation of tissue perfused for four hours shows early but definite evidence of myocardial ischemic damage involving the whole heart. Also observed were patchy and extensive contraction band formations, intense myocardial eosinophillia associated with smudging of the details of the fibers, and an undulating fiber formation. Control tissue processed for light microscopy promptly after sacrificing an animal showed normal morphology with none of these changes. Intact and open heart tissue, similar to the perfused hearts, released significant neutrophil chemoattractants. Similar activity was detected in the supernatant, whether cardioplegia or PBS was used.

The collected supernatants are centrifuged at about 1,000 rpm for five minutes or so to remove any whole cells or tissue debris. They are then subjected to ultrafiltration, such as by using Amicon filter membranes having a molecular weight cut-off of 100,000 to 300,000 daltons to initially separate and concentrate the factors. An average of 16–20 ml are filtered per membrane. Approximately 80–100 ul volume is retained on the top of the membrane as the retentate. Material collected above and below the filter were assayed for chemotactic activity and significant activity was recovered only in the retentate and not in the flowthrough material, thereby indicating that the low molecular weight factor remains predominantly associated with the co-factor carrier in the concentrated retentate. Membranes can be kept at −20° C. for up to six weeks without destroying the chemotactic activity. However, freezing the supernatant solutions prior to filtration destroys the chemotactic activity. Therefore, for storage purposes the supernatant solutions should be concentrated and dried using the ultrafilters prior to freezing.

Following the ultrafiltration or concentration process, the chemotactic factors are purified and further separated, preferably by using gel filtration high performance liquid chromatography, HPLC, having a molecular weight range of 1 to 300K daltons. The chromatographic fractions are then tested for neutrophil chemotactic activity.

Due to the small quantities available, the concentrated material is typically diluted prior to injection into the chromatographic column. The chromatographic fractionation yields two predominant peaks, the first of which includes the active fractions 1 to 10 with molecular weights from about 100,000 daltons to 500,000 daltons and more. These fractions also elute the highest protein levels. The chemotactically active fractions 15 to 23, at first believed to contain subunits or degradation products of the factors, have been found to contain the active low molecular weight form of the factor. These are believed to have a molecular weight of less than 5,000 but greater than 500 daltons. These two peaks or regions of chemotactic activity can be seen in FIGS. 4–7 but are best noted in FIG. 6. Using radio-labelled $LTB_4$, IL-8, and C5a, it has been found by standard radio immunoassay that these factors, which elute in substantially the same region, are not producing the effect found in the low molecular weight region.

As can be appreciated, other chromatographic processes may be used in place of the gel filtration HPLC. However, the sequential ultrafiltration/gel filtration analysis indicates that the activity observed in the high molecular weight range contains a mixture of the low molecular weight chemotactic factor and the weakly associated complex of that factor with a high molecular weight co-factor carrier. It is also believed that some disassociation occurs during separation in the chromatographic process.

Recent efforts have been focused on understanding the link between ischemical reperfusion and inflammation associated with open heart surgery, organ transplants, or similar procedures. Although it is generally postulated that during ischemia chemical signals are produced by injured tissue which initiate the recruitment of neutrophils, these signals had not been identified. Mediators, such as serum-derived complement system, break down products of fibrin clot, mediators released from activated immune cells and products produced when plasma is exposed to superoxide were postulated to be involved in this process. However, according to the present invention, it has been found that injured tissue will release factors that are quite different from serum-derived and immune cell-derived chemotactic factors such as C3a, C5a, $LTB_4$ and IL-8. It is also believed that the myocardial-derived factor is different from the superoxide dependent latent chemotactic factor present in extracellular fluids. These previously known factors fail to stimulate neutrophil degranulation. Unlike the superoxide dependent factor, the neutrophil chemotactic factors released from ischemic hearts are proteinaceous in nature and are not organic extractable, that is, they are not lipophillic and will stimulate neutrophil degranulation.

While the precise chemical structure of the factors has not been determined, a significant reduction in chemotactic activity was observed following treatment of the factor with the bacterial protease, Subtilisin, bound to agarose beads. Control studies have revealed that the reduction in chemotactic activity is not the result of the factors sticking to the agarose beads. Protein character is further indicated by a reduction in chemotactic activity when treated with either proteinase-K or carboxypeptidase-A, both for a period of 90 minutes at 37° C. Chemotactic activity dropped 58% and 64% respectively after such treatment. Reduction in chemotactic activity was also observed after heating to 56° C. and 100° C. for 30 to 60 minutes. Amicon ultrafiltration of the collected supernatants indicated that the majority of the activity, that is about 80%, exhibited high molecular weight values. The activity was not extractable by organic solvents such as ethyl acetate, suggesting that the chemoattractant is not leukotriene dependent. Radioimmuno assay, RIA, confirms this finding since very low levels of $LTB_4$ were detected.

The concentrated and separated factors have also been subjected to ion exchange columns and it has been found that the high molecular weight complexes exhibit a positive charge while the low molecular weight factor is either negatively charged or neutral.

The following examples are given in order that the effectiveness of the present invention may be more fully understood. These examples are set forth for the purpose of illustration only, and are not intended in any way to limit the practice of the invention. Unless otherwise specified, all parts are given by weight.

EXAMPLE I

Adult New Zealand white rabbits, weighing 3–4 kg were sacrificed with T-61 intravenously delivered by a marginal ear vein. The heart was removed and washed with saline. Ischemia of isolated rabbit hearts was induced by perfusing the heart with cold standard crystalloid cardioplegia under reduced flow or, by incubating the intact or open hearts with cold cardioplegia in a beaker or, by incubating myocardial segments with cold cardioplegia in a beaker, the perfusion and incubation being carried out at 4° C.

Perfusion of rabbit hearts was performed under reduced flow using a volume of 25 ml of cold non-oxygenated cardioplegia. At time intervals of five minutes, one, two, three and four hours, samples of 2 ml were removed to assay for the presence of neutrophil chemotactic factors. Four repeats were performed to evaluate the release of neutrophil chemotactic factors from ischemic profused rabbit hearts.

Intact hearts were incubated in a beaker with 20 ml freshly prepared carioplegia or phosphate buffer salt, PBS, at 4° C. At five minutes, one, two, three and four hours, samples of 1 ml were removed for chemotactic assay. The release of neutrophil chemoattractants was similarly assayed in the supernatants of rabbit hearts singly cut longitudinally. Three repeats were performed for each intact and open heart.

Rabbit heart segments were incubated with 7 ml cardioplegia or PBS at 4° C. At five minutes, one, two, three and four hours, supernatants were removed to assay for chemotactic activity. It was also determined whether neutrophil chemoattractants were released from myocardial segments obtained from isolated bovine and pig hearts. A minimum of four repeats was performed for each species. The results are shown graphically in FIGS. 1, 2 and 3.

Rabbit neutrophils were obtained from the peritoneal cavity of white New Zealand rabbits four hours after intraperitoneal injection of 400 ml of 0.15M sodium chloride containing 0.1% oyster glycogen. Neutrophil chemotactic activity was evaluated using modified Boyden chambers. A standard neutrophil chemoattractant, the synthetic tripeptide, f-Met-Leu-Phe, was the positive control for 100% chemotactic response while Hank's Balanced Salt Solution (HBSS) was the negative control for random migration.

Rabbit neutrophils were adjusted to a final density of $2.5 \times 10^6$ cells/ml in HBSS containing 0.1% of bovine serum albumin, BSA. A 140 ul volume of neutrophil suspension was placed in the top compartment of each chamber containing millipore membrane of porosity 8 um. The bottom compartment of the chamber contained 140 ul of f-Met-Leu-Phe, HBSS or serum samples. The chambers were then incubated for one hour at 37° C. in a 5% $CO_2$ atmosphere to permit cell migration across the membrane. Following incubation, filters were removed, fixed, stained and mounted on glass slides for counting using an image analyzer. Triplicate micropore filters were used for each test and three readings were taken at random for each filter. Cell migration response to putitive chemoattractants was expressed as percent maximum chemotactic response as set forth in FIGS. 1, 2 and 3.

To purify the chemotactic activity, the concentrated materials above the filter were diluted 1:10 with mobile phase (0.1M Na phosphate monobasic and 0.1M Tris - pH to 6.5 with phosphoric acid), then filtered through 0.45 um filter type HA. A volume of 250 ul of the pass through was injected to high performance liquid chromatography (HPLC) composed of two gel filtration columns, i.e., Bio-Rad TSK 50 (300,000 to greater than 1,500,000 daltons) and Bio-Rad TSK 250 (1,000 to 300,000 daltons). Fractions were collected from 10 minutes after injection to 30-35 minutes. Chart speed was 0.1 inches per minute. The flow rate was 1 ml/1 minute/fraction. The detector (Waters-Lambda Max 480) was set at 280 nm wave length. Freezing HPLC samples at $-20°$ C. destroys the chemotactic activity. For storage purposes, samples should be concentrated using membranes of cut off at 10,000 daltons. Membranes can then be kept at $-20°$ C. for up to six weeks.

To determine whether the observed leukocyte migration is due to increased directed migration, i.e., chemotaxis, or increased random migration, i.e., chemokinesis, a standard checkerboard analysis was performed. Varying amounts of supernatants were added to both the upper and the lower compartments of the Boyden chamber and incubated at 37° in a 5% carbon dioxide atmosphere for one hour.

Supernatant solutions of rabbit myocardial segments incubated with PBS for three hours were collected for initial biochemical characterization of neutrophil chemoattractants. These include:

1) Sensitivity to protease. Aliquots of agarose-conjugated Type VIII-A Subtilisin were washed twice with PBS. The packed gel was suspended in 500 ul of PBS and 100 ul volume was mixed with 900 ul supernatants. The suspension was incubated at 37° C. for 90 minutes. Myocardial supernatant was also incubated with plain agarose beads to control for non-specific sticking of chemotactic factors to the beads. At the end of incubation time, suspensions were centrifuged for five minutes at 5,000 rpm and the collected supernatants were assayed for chemotactic activity. This eliminates the interference of protease with neutrophil migration in the Boyden chambers.

2) Solubility in organic solvents. Supernatants were shaken with 100% ethyl acetate in a 1:3 ratio. The mixture was then centrifuged for five minutes at 5,000 rpm and the organic phase was removed and concentrated using nitrogen evaporation to prevent oxidation. Residues of the organic extracts were dissolved in PBS and assayed for chemotactic activity.

The chemotactic factors may be further purified by developing polyclonal antibodies for the factors and purifying the factors using affinity chromatography. In this instance, fractions 1 to 8 and 18–23 of HPLC were concentrated separately using filtration techniques with membranes having cut-offs at increments of 10,000 daltons. Rabbits were injected with the fractions for four consecutive weeks. Antibodies to the factors were then isolated from the serum of the immunized rabbits. Using the polyclonal antibodies for the chemotactic factors, materials were prepared for affinity chromatography and subsequent specific purification of neutrophil chemotactic factors released from ischemic tissue was obtained.

EXAMPLE II

To generate large quantities of cardiac derived neutrophil chemotactic factor, purification studies were carried out using pig hearts. Six to eight pig hearts were obtained weekly from a slaughterhouse and processed immediately. Hearts were singly cut longitudinally to expose the inner surfaces to buffer solutions. Hearts were then incubated with buffer, namely, Hank's Balanced Salt Solution (HBSS) at 4° C. for 30 min, two hours and four hours. At the end of incubation, supernatant solutions were collected and assayed as undiluted, and diluted 1:5 to 1:25 using HBSS for their levels of chemotactic activity, using modified Boyden chambers as described in Example I.

Effluent samples of 10 ml each were first concentrated using an Amicon ultrafiltration technique with a cut-off of 500 daltons. About 100 ul of the retentates were then fractionated on a gel filtration HPLC column of molecular weight range of 1-300 KDa. Phosphate-buffered saline (PBS) of pH 7.4 was used to elute the various fractions. Using modified Boyden chambers, chemotactic activity was assayed for all collected fractions as undiluted and diluted 1:5 and 1:25 in HBSS.

Cell migration in response to the putative chemoattractants is expressed as percent chemotactic response induced by f-MLP. Chemotactic index is defined as the product of the distance traveled in the filter and the cell number. A minimum of two chemotaxis experiments were performed for each serum sample collected. Samples were assayed in duplicate and cells migrated within the filters were counted in six different areas.

Supernatant solutions collected from singly cut pig hearts incubated at 4° C. for two hours were concentrated using Amicon ultrafiltration techniques with a cut-off of 100,000 daltons. Chemotactic activity was recovered only in the retentate and not in the flow-through.

Figure 5:
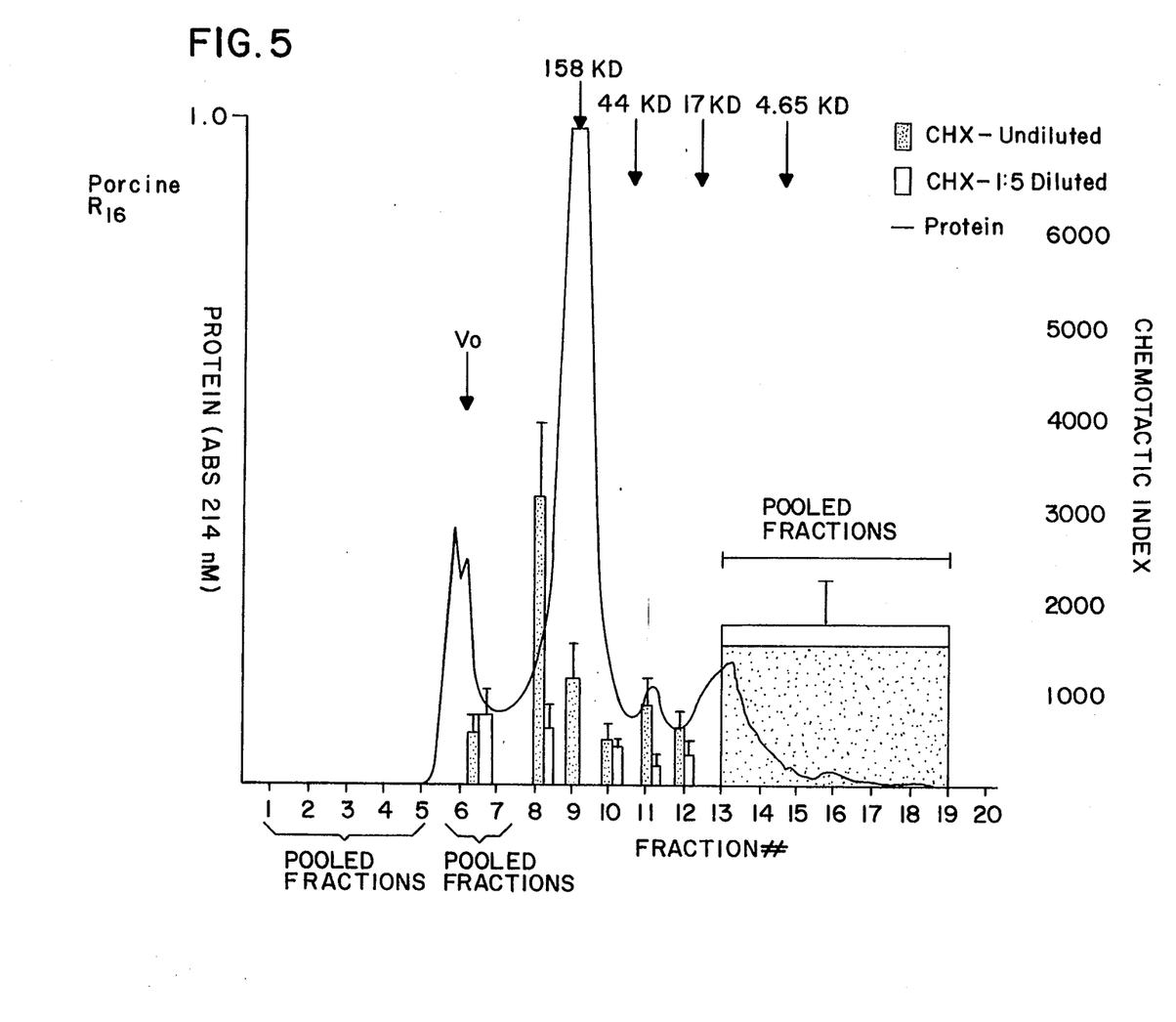
FIG. 5 is a graph showing neutrophil chemotactic activity and protein elution profile in various fractions isolated from test animals.

The retentates were then fractionated using a gel filtration high performance liquid chromatography (HPLC) column with a molecular weight range of 1–300 KDa. FIG. 5 is representative of six experiments and shows the neutrophil chemotactic activity and protein elution profile of the concentrates. A volume of 100 ul of the concentrate was employed in the column. Chemotactic activity was detected in two peaks or regions which eluted at a high molecular weight range of 100–300 KDa and a low molecular weight range of less than 5 KDa.

EXAMPLE III

Coronary sinus effluents were collected from six patients undergoing aortocoronary bypass and tested for the presence of other known chemotactic factors such as the immune-cell derived IL-8 and $LTB_4$. Samples taken prior to and during aortic cross-clamping as well as following cross-clamping showed no detectable IL-8 or $LTB_4$. Additional inflammatory mediators such as IL-2 and IL-6 were similarly undetectable indicating the absence of interleukins during cardiac arrest and during the early stage of reperfusion. Tests were also performed for the presence of the serium-derived chemotactic factor C5a in 12 additional patient samples. No detectable levels were observed.

Figure 6:
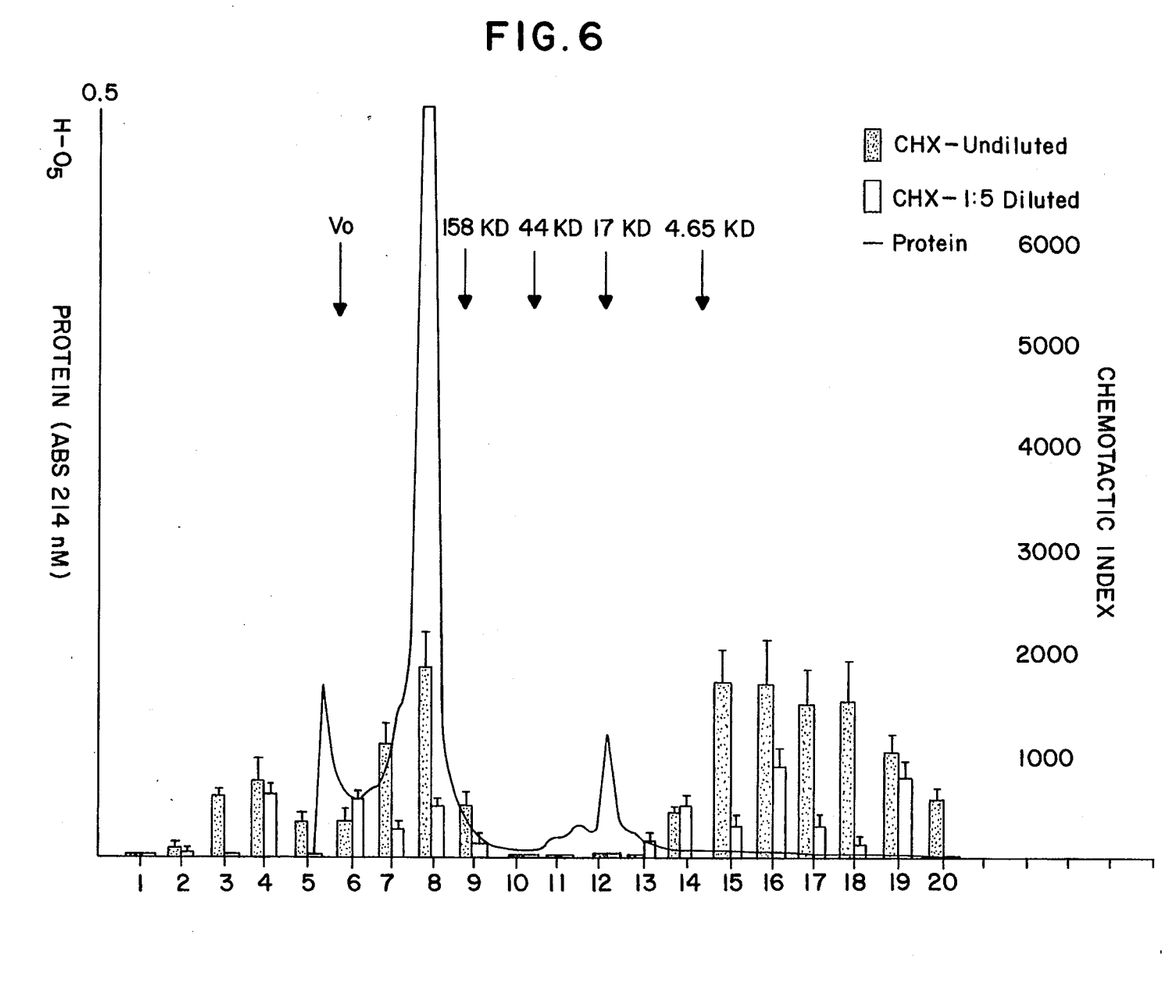
FIGS. 6 and 7 are graphs similar to FIG. 5 for fractions isolated from coronary sinus effluents of human patients during open heart surgery for myocardial revascularization.
Figure 7:
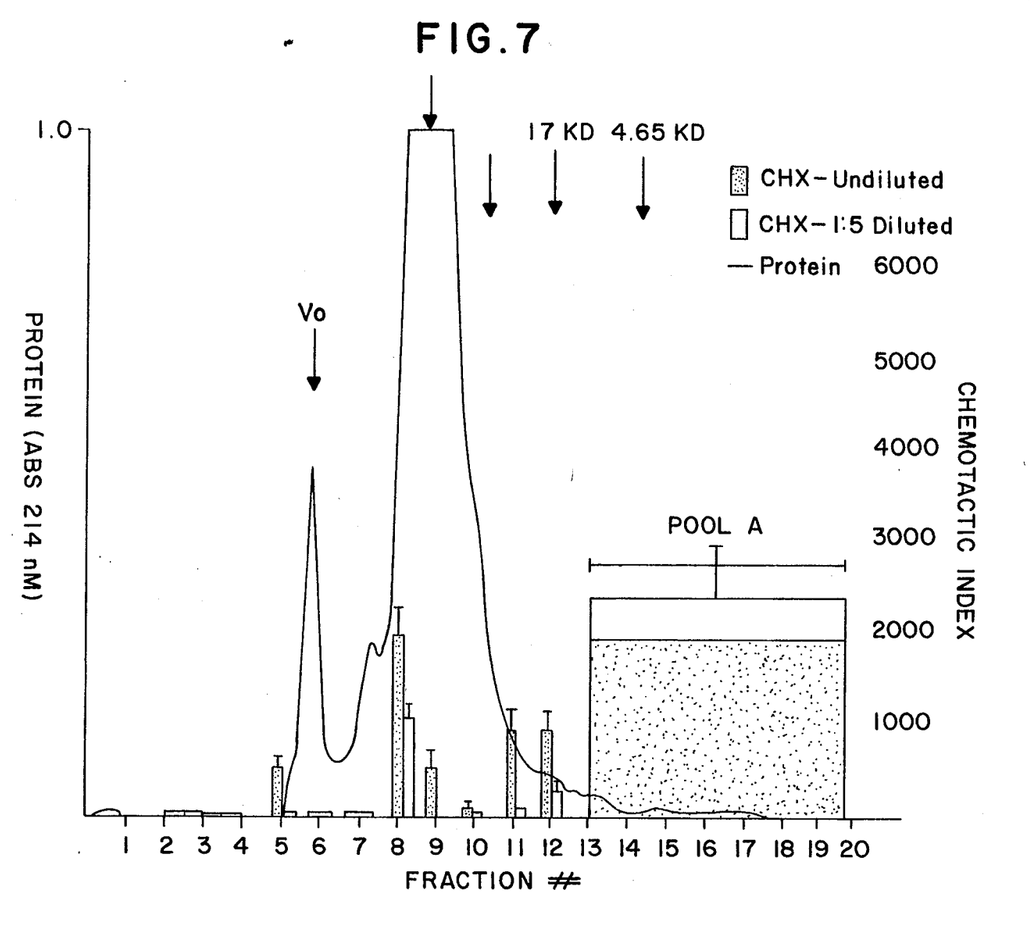

Having established the absence of IL-8, $LTB_4$ and C5a, the above-described purification experiments of Example II were repeated using coronary sinus effluents collected during one hour cardiac arrest from patients undergoing aortocoronary bypass. Starting effluent samples as well as retentates of the 100 KDa cutoff Amicon membranes were fractionated using the same type of gel filtration HPLC column and PBS buffer. As shown in FIG. 6 and FIG. 7 representative of 12 different patients, chemotactic activity was detected in peaks eluted at a correspondingly high molecular weight range of 100–300 KDa and a low molecular weight range of less than 5 KDa for both the starting samples (FIG. 6) and the retentates (FIG. 7).

Figure 8:
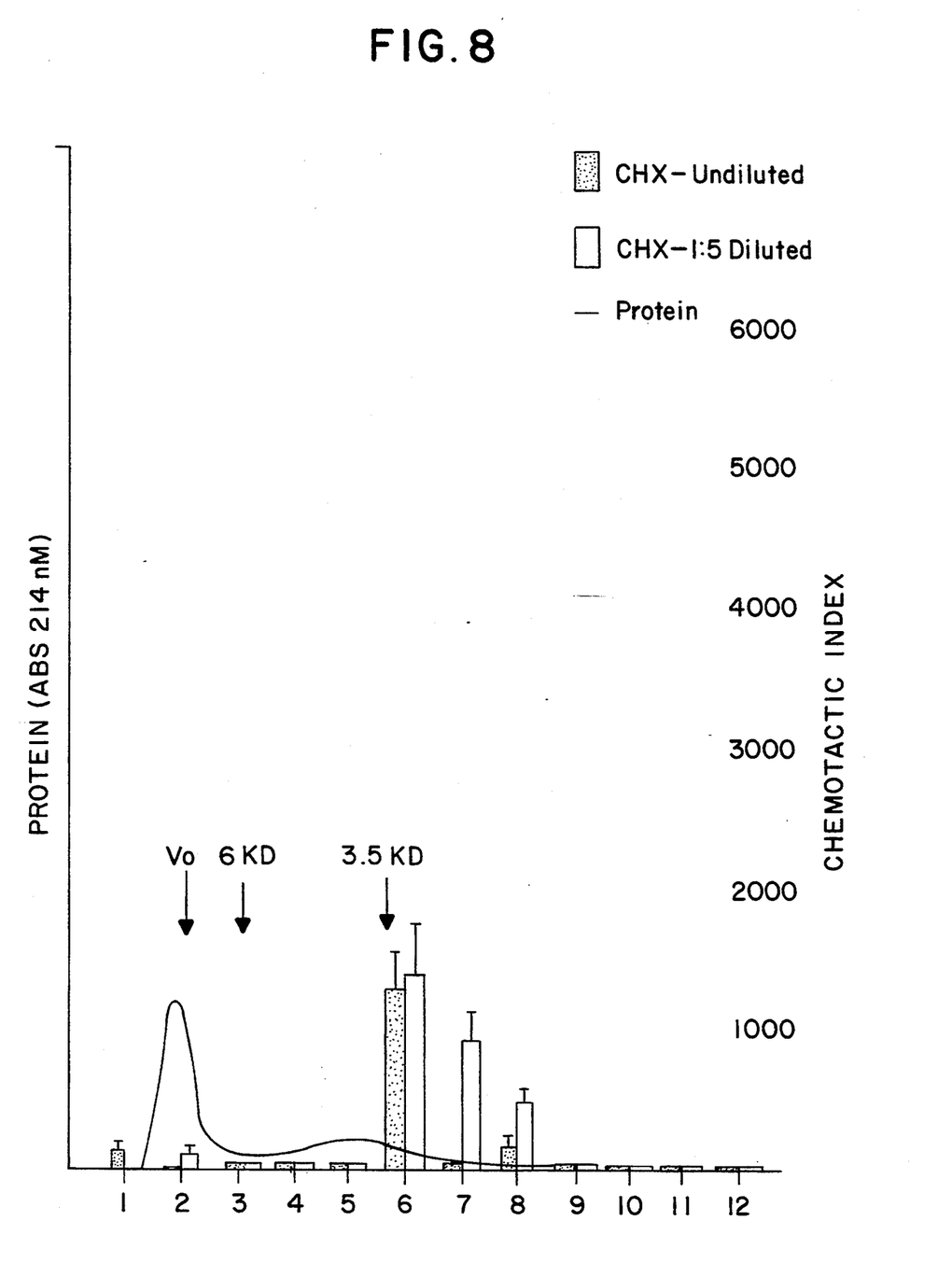
FIG. 8 is a graph similar to FIGS. 5-7 of fractions 13-20 of FIG. 7.

Since these results are similar to data previously obtained from pig hearts, further purification studies were performed using patient effluents. Fractions 13–20 of FIG. 7 of molecular weight less than 5 KDa were fractionated on a gel filtration HPLC column having a molecular weight range of 1–6 KDa, using Biorad-Econo Pac-6. As can be seen in FIG. 8, chemotactic activity representative of five different patients was detected in a peak eluted at approximately 3 KDa. Biochemical characterizations of this previously undescribed factor revealed that it is heat labile and protease sensitive in response to proteinase K, carboxypeptidase-A, indicating that this factor is "proteinaceous" in nature. The chemotactic index before and after each treatment is set forth in Table 1.

TABLE 1

NEUTROPHIL CHEMOTACTIC ACTIVITY
Chemotactic Index

| | Before Treatment | After Treatment | Reduction |
|---|---|---|---|
| Proteinase K | 3971 ± 325 | 1655 ± 135 | 58% |
| Carboxypeptidase-A | 3971 ± 325 | 1436 ± 135 | 64% |
| Heating | 3971 ± 325 | 2428 ± 174 | 39% |

The concentrated and fractionated retentate was also fed to an ion exchange HPLC column packed with a positive ion exchange resin, DEAE-3SW sold by Perkin-Elmer. The material was eluted using PBS at pH7.4 with 1M sodium chloride. The high molecular weight complex passed through the column with negligible retention thereby indicating its positively charged character while the low molecular weight factor was held in the column, indicating a negatively charged or neutral character.

EXAMPLE IV

Figure 9:
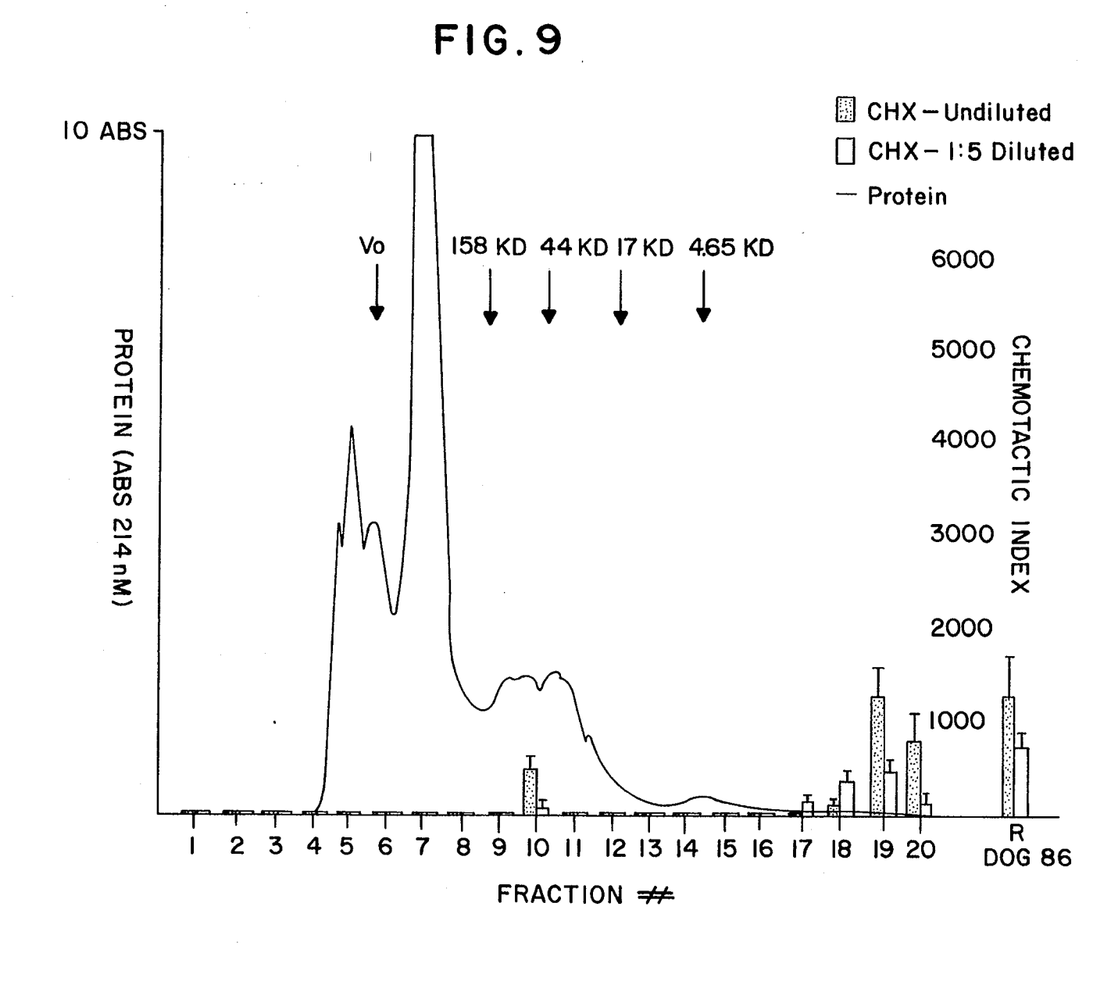
FIG. 9 is a graph similar to FIG. 7 of coronary sinus effluents from test animals.

Coronary sinus effluents were collected from canine hearts arrested by aortic cross clamping for one hour. Repeating the procedure of Example III, high chemotactic activity in the high and low molecular weight range are shown in FIG. 9 when concentrated samples were fractionated on the same type of gel filtration HPLC column as in Example III. These results indicate a similarity between the canine neutrophil chemotactic factor and the above-described pig and human factors.

As can be seen from the foregoing, the mediators of the present invention likely provide the initial injury signal which stimulate neutrophil migration toward the infarcted area during subsequent reperfusion. It is believed that these factors may be used to control the infiltration of neutrophils associated with myocardial ischemia.

As will be apparent to persons skilled in the art, various modifications, adaptations and variations of the foregoing specific disclosure can be made without departing from the teachings of the present invention.

I claim:

1. A partially purified and isolated biological mediator of immune function for stimulating neutrophil activity, said mediator being released upon tissue injury and consisting essentially of a protein complex of a neutrophil chemotactic factor and a co-factor carrier weakly ionically associated therewith wherein the protein complex has the following physico-chemical and biochemical characteristics: a molecular weight of about 100,000 to 300,000 daltons with said factor having a molecular weight within the range of about 500 to 5,000 daltons, protease sensitivity, heat instability, non-leukotriene, non-interleukin, non-serum derived, non-immune cell derived and will stimulate neutrophil degranulation.

2. The biological mediator of claim 1 wherein the level of neutrophil chemotactic activity of the mediator is 5% to 700% the maximum chemotactic response of the synthetic tripeptide f-Met-Leu-Phe used as a standard.

3. The biological mediator of claim 1 wherein the mediator in dry concentrated form will withstand −20° C. without losing its chemotactic activity for about four to six weeks.

4. The biological mediator of claim 1 obtained from mammalian cardiovascular tissue.

5. The biological mediator of claim 1 obtained from tissue selected from the group consisting of human, rabbit, bovine and pig tissue.

6. The biological mediator of claim 1 wherein the complex is positively charged.

7. The biological mediator of claim 1 wherein the factor is weakly negatively charged or neutral.

8. The biological mediator of claim 1 wherein the factor has a molecular weight of about 3,000 daltons.

9. A purified and isolated biological mediator of immune function for stimulating neutrophil activity, said mediator being a protein released upon tissue injury and having the following physico-chemical characteristics: a molecular weight within the range of about 500 to 5,000 daltons, protease sensitivity, heat instability, non-leukotriene, non-interleukin, non-serum derived, non-immune cell derived and will stimulate neutrophil degranulation.

10. The biological mediator of claim 1 wherein the factor is weakly negatively charged or neutral.

11. The biological mediator of claim 1 wherein the factor has a molecular weight of about 3,000 daltons.

* * * * *

UNITED STATES PATENT AND TRADEMARK OFFICE
CERTIFICATE OF CORRECTION

PATENT NO. : 5,403,914
DATED : April 4, 1995
INVENTOR(S) : Salwa A. Elgebaly

It is certified that error appears in the above-indentified patent and that said Letters Patent is hereby corrected as shown below:

Column 12,

Claim 10, line 1, delete "1" and replace with -- 9 --.

Claim 11, line 1, delete "1" and replace with -- 9 --.

Signed and Sealed this

Fifteenth Day of October, 1996

Attest:

BRUCE LEHMAN

Attesting Officer          Commissioner of Patents and Trademarks